United States Patent [19]
Cohen et al.

[11] Patent Number: 4,815,964
[45] Date of Patent: Mar. 28, 1989

[54] ELECTRODE HAVING LEAD WIRE ATTACHMENT

[76] Inventors: Joel Cohen; Esther R. Cohen, both of 1020 NW. 99 Ave., Plantation, Fla. 33322

[21] Appl. No.: 78,428
[22] Filed: Jul. 27, 1987
[51] Int. Cl.[4] ............................................. A61B 5/04
[52] U.S. Cl. ................................................... 128/641
[58] Field of Search ............... 128/639, 640, 641, 644, 128/798, 802, 803

[56] References Cited

U.S. PATENT DOCUMENTS

| | | | |
|---|---|---|---|
| 4,072,388 | 2/1978 | Dunn | 339/103 R |
| 4,265,253 | 5/1981 | Abraham | 128/803 X |
| 4,331,153 | 5/1982 | Healy | 128/641 |
| 4,332,257 | 6/1982 | Ayer | 128/640 |
| 4,463,999 | 8/1984 | Knickerbocker | 339/75 P |
| 4,653,501 | 3/1987 | Cartmell et al. | 128/649 |

*Primary Examiner*—Lee S. Cohen
*Attorney, Agent, or Firm*—John Cyril Malloy

[57] ABSTRACT

In one embodiment, the electrode is used in conjunction with a lead wire and a head that attaches to the electrode. The electrode itself includes first and second main face each having, among other things, a central zone. The central zone of each face is made of an electrically conductive material such that electrical current flows between the first and second main faces. The first face is releasably adhered to the skin of the patient or wearer. Radially outboard of the central zone mounted on the second main or outer face of the electrode is an elongate member. A first portion of the elongate member is attached to the second main face. The second portion of the elongate member is movable with respect to the first portion and enables the tight embrace of the head when the head is in the electrical engagement with the conductive material of the first main face. The elongate member includes a latch means to tie or strap the head onto the second main face of the electrode.

3 Claims, 1 Drawing Sheet

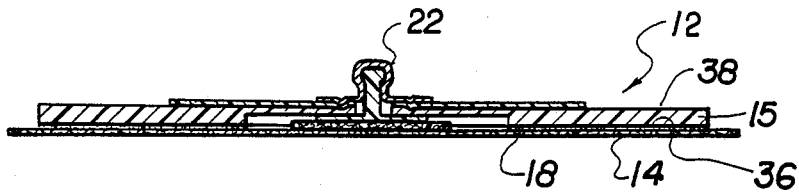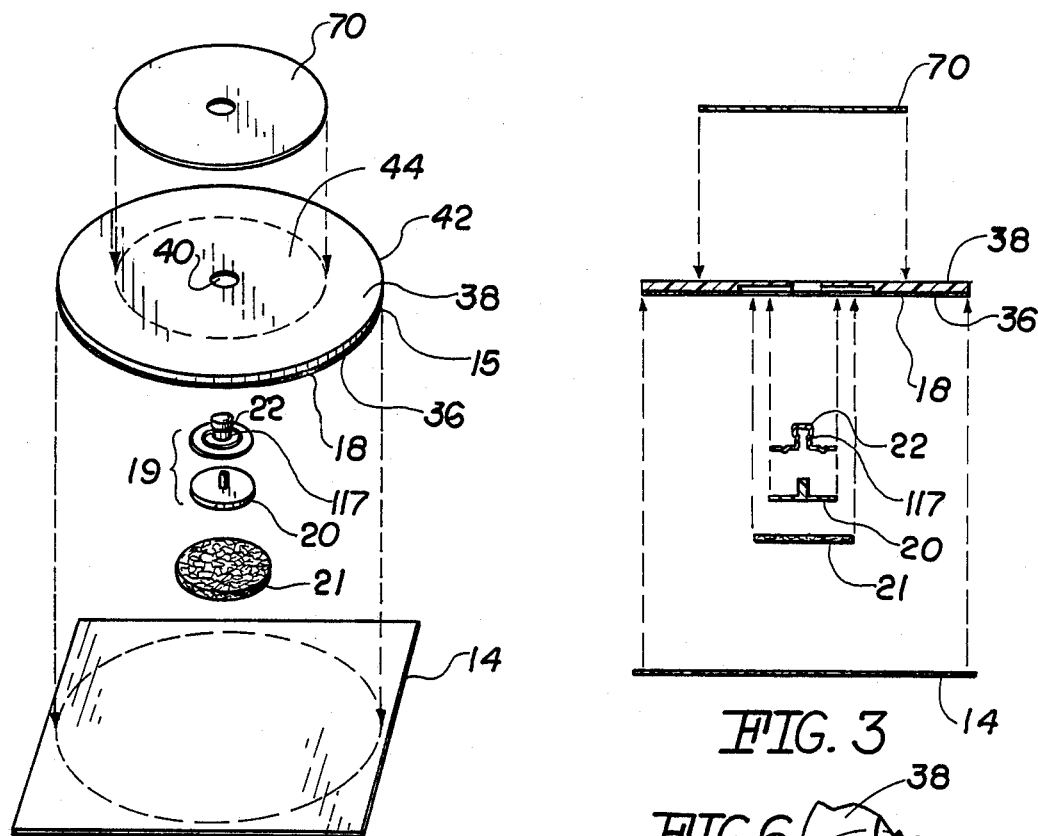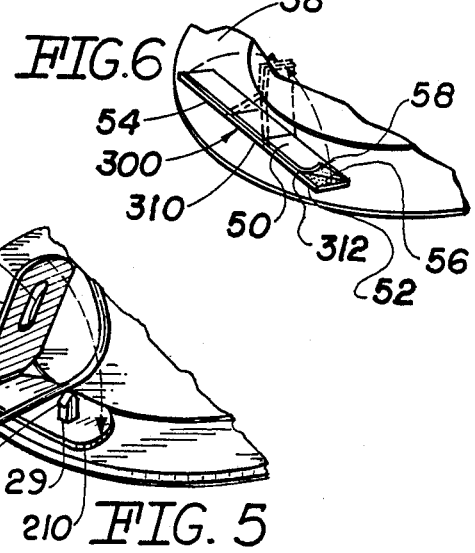

ELECTRODE HAVING LEAD WIRE ATTACHMENT

BACKGROUND OF THE INVENTION

The present invention relates to an improved electrode that is releasably attached to a person in order to detect bodily functions, such as electrocardiogram (ECG) signals, wherein the electrode includes an attachment mechanism for the head extension extending from the electrode head.

In medical applications it is sometimes necessary to releasably attach electrodes to the bodies of patients in order to monitor physiological characteristics such as heart rate. Typically, electrodes are attached to the body of a patient and the electrodes pick up the electrical signals generated by the body. These electrodes are connected to electrode lead wires via an electrode head. The other end of the lead wires are connected to machinery that processes these electrical signals and produces data characteristic of the body function being monitored. Typically, the electrode head is releasably attached to the electrode which in turn is adhered to the patient's skin. At times, the patient is required to walk or run on a treadmill while the physician or medical technician monitors the appropriate body function via the electrodes attached to the patient's skin. In this situation, the lead wires and electrode heads can move since the patient himself is moving. This movement sometimes causes the head to detach from the electrode thereby corrupting the sensing of electrical signals and adversely affecting the quality of the data obtained during this physical test of the patient. At other times when the head moves or rotates with respect to the electrode, an electrical artifact or signal distortion is generated by the movement which corrupts the data being collected.

U.S. Pat. No. 4,332,257 to Ayer discloses a medical clip and an electrode construction wherein the head attached to the lead wire is inserted below an elastic bridge thereby trapping the head between the undersurface of the bridge and the outer surface of the electrode. The extensive end of the head has a releasable clip that attaches to a pin that runs from the outer surface of the electrode to the inner surface that is proximate the patient's skin. The bridge does not stop lateral movement of the electrode. U.S. Pat. No. 4,331,153 to Healy discloses a disposable EKG electrode. The electrode is elliptically shaped and has an arcuate cut through one end of the shape which enables the lead wire to be placed underneath the slice or cut and wrapped around the shape in a double loop in order to secure the lead wire to the electrode. U.S. Pat. No. 4,653,501 to Cartmell, et al. discloses a medical electrode with a reusable conductor. Generally, the electrode includes a flap cover that opens to expose the top surface of the electrode. The head is placed in a central region in the electrode and the flap cover is lowered to thereby encase the head and the lead wire. U.S. Pat. No. 4,463,999 to Knickerbocker discloses an electrical hold down connector that connects a multiple electrical cable connector together via a strap. U.S. Pat. No. 4,072,388 to Dunn discloses an anti-snag device for electrode lead clips.

OBJECTS OF THE INVENTION

It is an object of this invention to provide an improved electrode that is capable of monitoring a patient on a long term basis without having the head detach from the electrode.

It is another object of the present invention to avoid the use of taping the lead wire and head onto the electrode by using a lead wire attachment mechanism.

It is a further object of the present invention to have an attachment mechanism that can accommodate different types of electrode heads.

It is an additional object of the present invention to provide an attachment mechanism that straps or wraps around many different sizes of heads therefore enabling the universal use of electrode heads with this type of electrode.

It is a further object of the present invention to secure the electrode head to the electrode thereby minimizing the possibility of an electrical artifact being generated in the lead wire due to movement of the lead wire with respect to the electrode.

SUMMARY OF THE INVENTION

In one embodiment, the electrode is used in conjunction with a lead wire and a head that attaches to the electrode. The electrode itself includes a first and second main face each having, among other things, a central zone. The central zone of each face is made of an electrically conductive material such that electrical current flows between the first and second main faces. The first face is releasably adhered to the skin of the patient or wearer. Radially outboard of the central zone and mounted on the second main face of the electrode is an elongate member. A first portion of the elongate member is attached to the second main face. The second portion of the elongate member is movable with respect to the first portion and enables the tight embrace of an electrode head when the head is in the electrical engagement with the conductive material of the first main face. The elongate member includes a latch means to tie or strap the head onto the second main face of the electrode.

BRIEF DESCRIPTION OF THE DRAWINGS

Further objects and advantages of the present invention can be found in the detailed description of the preferred embodiments when taken in conjunction with the accompanying drawings in which:

FIG. 1 illustrates a cross-sectional view of an electrode;

FIG. 2 illustrates an exploded view of the electrode;

FIG. 3 illustrates a further exploded cross-sectional view of the electrode;

FIG. 4 illustrates one embodiment of the attachment mechanism placed on the outboard, outer, or second main face of the electrode;

FIG. 5 illustrates a second embodiment for the attachment mechanism for the lead wire; and, FIG. 6 illustrates a third embodiment for the attachment of the lead wire to the electrode.

DETAILED DESCRIPTION OF THE PREFERRED EMBODIMENTS

The present invention relates to an improved electrode having an attachment mechanism that attaches the lead wire of an electrode head to the outer main face of the electrode.

FIGS. 1, 2 and 3 will be discussed concurrently herein where like numerals designate similar items throughout these and the remainder of the figures. Electrode 12 includes a removable liner 14 that provides a shield for adhesive 18 on the first main face 36 of the electrode. Liner 14 can be a paper material including waxed paper or plastic material. Electrode 12 is principally a sheet 15 of flexible material having a central zone 40, an intermediate zone 44 and an outer peripheral edge 42. The second main face 38 is outboard or is the outside surface of electrode 12 when the electrode is adhered to the skin of the patient or wearer. Typically, a snap type mechanism 19 protrudes through central zone 40 and is made up of an electrically conductive material 22 open to the outer or second main face 38 and an electrically conductive material 20 open to the inner or first main face 36 of electrode 12. As best shown in FIG. 1, electrical conductor 22 protrudes well beyond face 38 and to accommodate electrical energy flow via conductor 20 from first face 36 to second face 38. A cover 70 is affixed to second face 38 at intermediate zone 44. To protect the integrity of conductor 20, a shield 21 is interposed between first face 36, that carries adhesive 18, and removal liner 14.

As shown in FIG. 4, lead wire 14 terminates with an electrode head 30. The head shown in FIG. 4 is a simple clip-on device having handles 110 and 112 that, when compressed towards each other, open jaw faces 114 and 116 thereby releasing the jaw faces from post 117 that is part of the electrical conductors 20 and 22. Other snap-on heads may be utilized such as a unitary, plastic, dome-like, snap-on head.

The attachment means shown in FIG. 4 is a tie wire coated with plastic or other type of non-conductive material. The attachment means is an elongate member 26 having a first fixed portion 27 that is fixed to cover 70 on outer, second main face 38. Fixed portion 27 is radially displaced outboard of central zone 40. The elongate member 26 includes a second movable portion 28 that is movable with respect to the first portion. Movable portion 28 can tightly embrace head extension 13 when head 30 is in electrical engagement with conductor 22. In FIG. 4 elongate member 26 includes a third portion 34 extending from the fixed first portion opposite from the movable second portion 28. The second and third portions are means to releasably secure the head extension therebetween. This is also an inter-engaging means that tightly embraces the head extension and in this case the clamping arms 110 and 112 to guard against rotational movement of electrode head 30 and lifting movement of lead wire 14 and head 30 relative to electrode 12.

FIG. 5 illustrates another embodiment of the attachment mechanism. Elongate member 200 includes fixed portion 210 having an upstanding stud 29 on it. The elongate member also includes a movable portion 212 having a recess 33 in it. Stud 29 includes an enlarged distal end zone 31 that is companionately sized with respect to recess 33 to allow forceable entry of end zone 31 therein to lock the portions in tight embrace around lead wire 14. A ball and socket fit may be preferable. In both the instances of FIGS. 4 and 5, the elongate members 26 and 200 can be glued via an adhesive to either cover 70 in FIG. 4 or outer surface 38 in FIG. 5.

FIG. 6 shows a further embodiment of the attachment mechanism utilizing elongate member 300. Member 300 has an outer face 50 and inner face 52. Inner face 52 confronts and is attached to second main face 38 of the electrode. The elongate member includes fixed portion 310, movable portion 312, and a third movable portion 54 that extends from the fixed portion 310 opposite from the second movable portion 312. The outer face 50 of the member includes an adhesive means 56 for adhering second portion 312 and third portion 54 together thereby tightly embracing the head extension therebetween. A liner 58, possibly made of waxed paper, protectively covers adhesive means 56 on the outer face of elongate member 300.

Modification and changes within the scopes and spirit of the present invention are meant to be encompassed by the claims appended hereto.

What is claimed is:

1. An electrode for use in connecting an assembly including a lead wire electrically connected to a head to a wearer, said electrode being of the type having:

a first and a second main face, each face having:

a central zone, an outer peripheral edge, and an intermediate zone;

said central zone of each main face being of electrically conductive material and the conductive material of each face at all times being in electrical engagement to accommodate electrical energy flow between the first and second main faces, adhesive means on said first main face to adhere the first main face to the skin of said wearer;

removable liner means normally overlaying said central zone of said first main face and the adhesive means and removable to expose the adhesive means and the electrically conductive material of the first main face to confront the skin of said wearer when being used, an elongate member having a first portion and a second portion, means to fix said first portion to said second main face radially displaced outboard of said central zone with said second portion being movable with respect to said first fixed portion to tightly embrace said lead wire when the head is in electrical engagement with the electrically conductive material of the second main face;

said elongate member including mutually interengaging means on the portions to releasably maintain the tight embrace of said portions to guard against rotational movement and lifting movement of said lead wire and head relative to the electrode and to maintain the head in electrical engagement with the electrode.

2. The device as set forth in claim 1 wherein said means to releasably maintain comprises an upstanding stud on said first fixed portion, said stud having an enlarged distal end zone and said second portion having a recess companionately sized for forceable entry of the distal end zone therein to lock the portions in tight embrace of a lead wire when disposed therebetween in use.

3. The device as set forth in claim 1 wherein said means to fix comprises an adhesive material secured in interconnecting relation to said first portion and said second main face.

* * * * *